(12) United States Patent
Kumar

(10) Patent No.: US 7,967,811 B2
(45) Date of Patent: Jun. 28, 2011

(54) BALLOON CATHETER WITH MANUALLY OPERATED VALVE AND ASPIRATOR

(76) Inventor: Anil B. Kumar, Bloomfield Hills, MI (US)

(*) Notice: Subject to any disclaimer, the term of this patent is extended or adjusted under 35 U.S.C. 154(b) by 603 days.

(21) Appl. No.: 11/973,139

(22) Filed: Oct. 5, 2007

(65) Prior Publication Data
US 2008/0114338 A1    May 15, 2008

Related U.S. Application Data

(60) Provisional application No. 60/849,667, filed on Oct. 5, 2006.

(51) Int. Cl.
*A61M 27/00* (2006.01)
(52) U.S. Cl. .............. 604/544; 604/99.02; 604/99.04
(58) Field of Classification Search .......... 604/99.02, 604/99.04, 544
See application file for complete search history.

(56) References Cited

U.S. PATENT DOCUMENTS

| | | | | |
|---|---|---|---|---|
| 3,211,151 A | * | 10/1965 | Foderick et al. | 604/97.02 |
| 4,245,639 A | * | 1/1981 | La Rosa | 604/97.02 |
| 4,306,705 A | * | 12/1981 | Svensson | 251/149.9 |
| 4,571,239 A | * | 2/1986 | Heyman | 604/544 |
| 5,141,503 A | * | 8/1992 | Sewell, Jr. | 604/317 |
| 5,190,046 A | * | 3/1993 | Shturman | 600/463 |
| 6,176,843 B1 | * | 1/2001 | DiCaprio et al. | 604/99.03 |
| 7,291,139 B2 | * | 11/2007 | Gershowitz | 604/509 |
| 2004/0044307 A1 | * | 3/2004 | Richardson et al. | 604/102.01 |

* cited by examiner

*Primary Examiner* — Tatyana Zalukaeva
*Assistant Examiner* — Benedict L Hanrahan
(74) *Attorney, Agent, or Firm* — The Weintraub Group, P.L.C.

(57) ABSTRACT

A Foley type catheter of the type including an elongated flexible tube and an inflation lumen, the distal end of the tube being provided with a membrane that is inflated into a balloon by fluid passage though the lumen, wherein to retain the distal end interiorly of a bladder, and a drainage eye, wherein to enable the catheter to drain urine therefrom. The proximal end of the tube is provided with a fluid control valve and a fluid pump, each hand operated as desired. The pump is in the form of a squeeze bulb and/or aspirator and adapted to deform to supply and/or withdraw fluid into and from the lumen and selectively inflate/deflate the membrane. In one embodiment, the pump is in the shape of a pleated bellows that is axially collapsed and end walls forced together and into a suction cup like retaining engagement, and a coil spring acts to restore the shape.

9 Claims, 2 Drawing Sheets

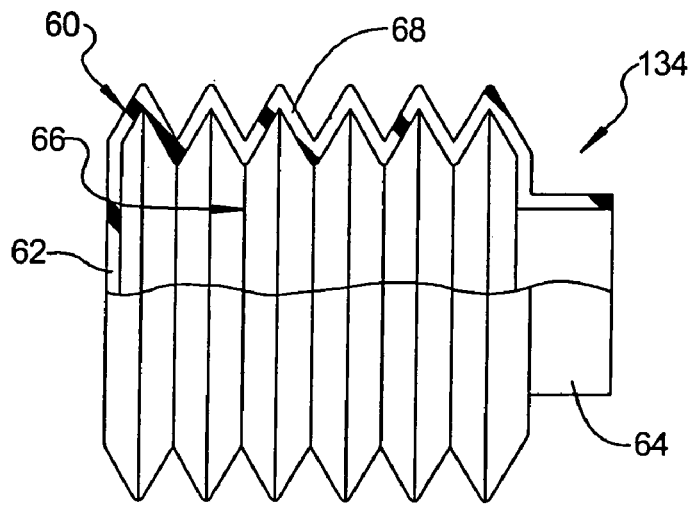
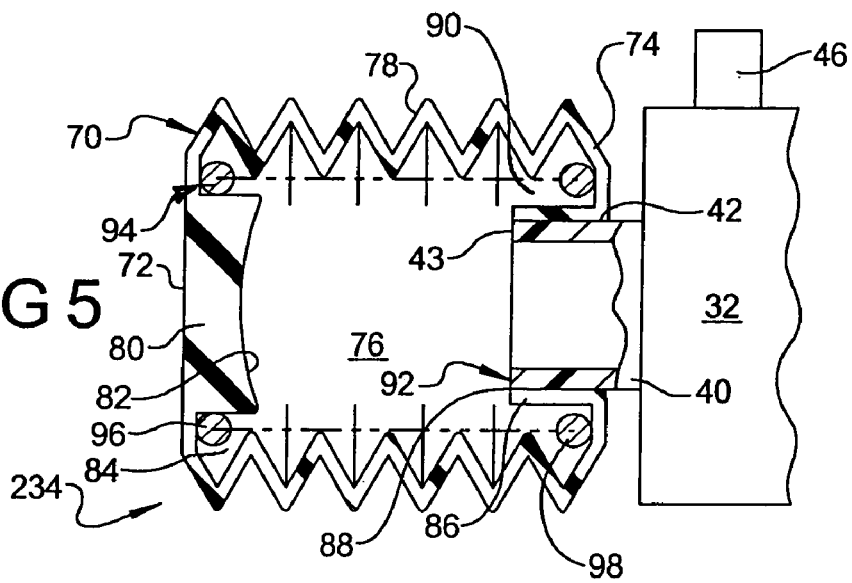
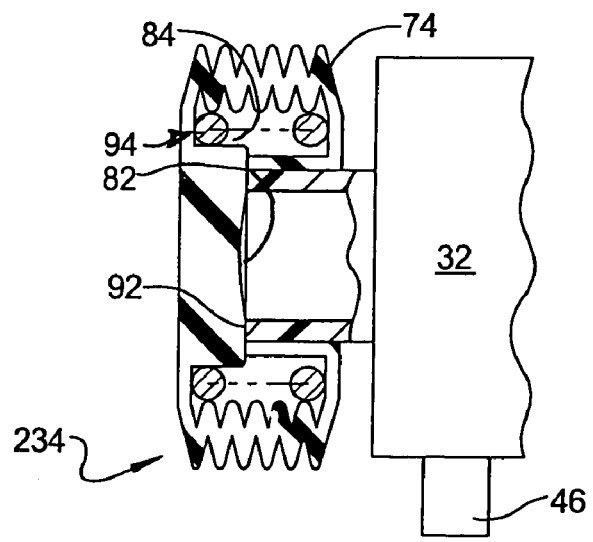

BALLOON CATHETER WITH MANUALLY OPERATED VALVE AND ASPIRATOR

CROSS-REFERENCE TO RELATED APPLICATIONS

This Application claims the benefit of U.S. Provisional Application No. 60/849,667, filed Oct. 5, 2006, the disclosure of which is incorporated herein in its entirety.

BACKGROUND OF THE INVENTION

1. Field of the Invention

The present invention relates to a Foley type catheter wherein the distal end of a flexible tube is provided with an inflatable balloon to retain the distal end interiorly of a bladder and enable the catheter to drain urine therefrom, and more particularly, to a such a catheter wherein the proximal end is provided with a valve device and squeeze bulb and/or aspirator pump, each hand operated, to selectively inflate and deflate the balloon, respectively, to retain the distal end interiorly of the bladder or other organ and permit removal of the distal end therefrom.

2. Description of the Prior Art

Balloon catheters often have a flexible shaft, including a tubular basic body with a distal end and a proximal end, a lumen extending between the ends, as well as a balloon affixed to the shaft near the distal end that is connected with the lumen. Such a basic balloon catheter is generally known, whereby the dimensions of the balloon and the tubular basic body are selected such that the balloon catheter can carry out a therapeutic treatment.

For example, a Foley catheter drains urine from the bladder. In operation, the balloon end of the tube is inserted into the bladder, whereupon the balloon must be inflated. Typically, to accomplish this, a medical worker fills a syringe with a measured quantity of fluid and injects this fluid into the lumen. The fluid inflates the balloon and the balloon retains the distal end inside the bladder.

Desirably the catheter would enable a homebound user, or caregiver, the ability to inflate the catheter without the need for a special syringe. Additionally, a catheter should not require the need of a caregiver filling a syringe with a measured supply of inflation fluid.

Desirably a catheter would be self-contained and enable a homebound user, or caregiver, the ability to deflate and reinflate the catheter should a homebound need arise for removal and reinsertion of the catheter.

Various catheter arrangements have been proposed, such as illustrated in U.S. Pat. Nos. 1,334,237; 2,032,859; 3,211,150; 3,275,001; 3,401,698; 3,818,903; 3,841,319; 4,101,342; 4,598,707; 4,614,188; 5,342,304; and 6,193,680.

These arrangements are listed in recognition of the duty of disclosure of related subject matter, which may be relevant, under 37 CFR 1.56.

While the arrangements shown in each of these patents is believed to have provided a solution to a specific problem there described, the field is always desirous of improvements in the art and it is to that need that the present invention is drawn.

An object of the present invention is the provision of a Foley catheter that includes an arrangement wherein a specially configured valve is combined with a hand operated squeeze bulb and/or aspirator pump to introduce or withdraw saline or other fluid solution into and from inflating relation with a catheter balloon.

Another object of this invention is the provision of a catheter wherein a squeeze bulb and/or aspirator pump or the like snaps into place with a sealing valve to enable inflation as well as deflation of the catheter.

Yet another object of this invention is the provision in a catheter a manually controlled fluid control valve in combination with an aspirator pump, the pump being a pleated accordion type of bellows that is axially collapsible/expandible.

Another object of this invention is the provision of a coil spring in the fluid reservoir of a pleated accordion bellows aspirator pump, the spring and bellows compressing axially to introduce balloon inflating liquid into the catheter lumen and expanding to assist in withdrawal of the balloon inflating liquid.

Yet another object of this invention is provision of a simple balloon catheter apparatus, the balloon of which being capable of being inflated and/or deflated by the user in situ, such as at home, and without the need for medical caregivers.

SUMMARY OF THE INVENTION

According to this invention, there is provided a balloon catheter for performing a medical treatment on a patient, comprising:

a flexible catheter shaft, with a tubular basic body having distal and proximal ends, and defining an inflation lumen extending between the ends; the proximal end defining a drain funnel;

a balloon affixed to the catheter shaft near the distal end, such that the balloon communicates with the inflation lumen; the balloon having an inflated state and a deflated state;

a squeeze bulb having an outlet stub and a reservoir for discharging inflation fluid stored in the reservoir; and a valve connected to the distal end, said valve connecting to the outlet stub of the squeeze bulb and communicating balloon inflating fluid from the reservoir to the inflation lumen, said valve including a valve plate having a central opening and selectively movable between a closed first position and an open second position; such that the valve plate in the closed position moves the plate opening into a position that prevents fluid flow from the proximal end through the inflation lumen and to the balloon, and in the open position moves the plate opening into a position that permits fluid flow to selectively inflate or deflate the balloon.

According to a preferred embodiment, the valve includes a housing, said housing having opposed pairs of first and second endwalls, respectively, and an interior chamber, and a supply tube having first and second ends, and wherein said valve plate is movable in a first direction between said first end walls;

said catheter shaft and supply tube are connected to one and the other of said second end walls and disposed on an axis transverse to said first direction, the proximal end said catheter shaft is disposed in said interior chamber and in juxtaposed relation to said valve plate, the first end of said supply tube is disposed in said interior chamber and in juxtaposed relation with said valve plate, and the second end of said supply tube is connected to the outlet stub of said squeeze bulb.

According to this invention, the squeeze bulb may comprise an aspirator pump, adapted to collapse, when supplying inflation liquid to inflate a membrane into balloon shape, and then, substantially simultaneously, expand and snap back into its original shape, sucking balloon inflating liquids outwardly and deflating the balloon.

In a particular aspect, in another preferred embodiment, a catheter assembly, comprising a catheter body having a lumen extending from a proximal end thereof through at least a portion of the catheter body, the catheter body being provided with a balloon secured to an exterior surface thereof and expandable between a relaxed state and an expanded state in response to a positive fluid pressure between the exterior and the interior of the lumen, a balloon inflation aperture fluidly interconnecting the lumen and the interior of the balloon, and a fluid discharge aperture for discharging fluid from the lumen, a fluid regulating valve provided with an inlet and an outlet and a manually operable closure member, the outlet fluidly connected to the inflation aperture and the closure member mounted for movement between open and closed positions, respectively, for permitting and preventing fluid to pass between the inlet and the outlet, and a manually operable aspirator pump fluidly connected to the inlet, said aspirator comprising a generally cylindrical bellows of the pleated type and defining a variable hollow chamber.

According to this preferred embodiment, a coil spring is mounted in the chamber for biasing the opposite ends of the bellows in opposite directions.

Also and according to this preferred embodiment, the aspirator pump includes opposite end walls that form, at least in part, mating end faces, which are sealingly mated with one another and form a suction cup like retention with one another when manually pressed together and the valve is in the closed position.

Further, the aspirator pump may comprise a ball-shaped squeeze bulb.

Depending on the application, the squeeze bulb and/or aspirator pump is removably and/or non-removably connected, at least in part, to the supply tube and/or the control valve.

Preferably, the material of the squeeze bulb and/or aspirator pump is comprised of a material that is impermeable to liquids, and resilient and flexible, such as provided by a self-restoring rubber and/or like elastomer, which will operate to restore the deformed member back into an original undeformed shape.

Preferably, the valve housing is comprised of a material that is impermeable to liquids, and the valve plate is planar and movable between and in generally parallel relation to the first end walls and between said first and second positions by a hand operated pushing motion.

The present invention will be more clearly understood with reference to the accompanying drawings and to the following Detailed Description, in which like reference numerals refer to like parts and where:

BRIEF DESCRIPTION OF THE DRAWINGS

FIG. 4 is a side view, partially broken away and in section, of an alternate embodiment of a squeeze bulb, in the form of an aspirator pump, used as a suction device with the control valve herein; and FIGS. 5 and 6 are side views, partially broken away and in section, of an alternate embodiment of an aspirator pump used with the control valve herein, with FIG. 5 showing the aspirator pump in an extended state, such as prior to discharging inflating fluid from a fluid reservoir thereof into the balloon, and FIG. 6 showing the aspirator pump in a compressed state, such as following discharge of balloon inflating fluid from the reservoir thereof.

DETAILED DESCRIPTION OF THE PREFERRED EMBODIMENT

Figure 1:
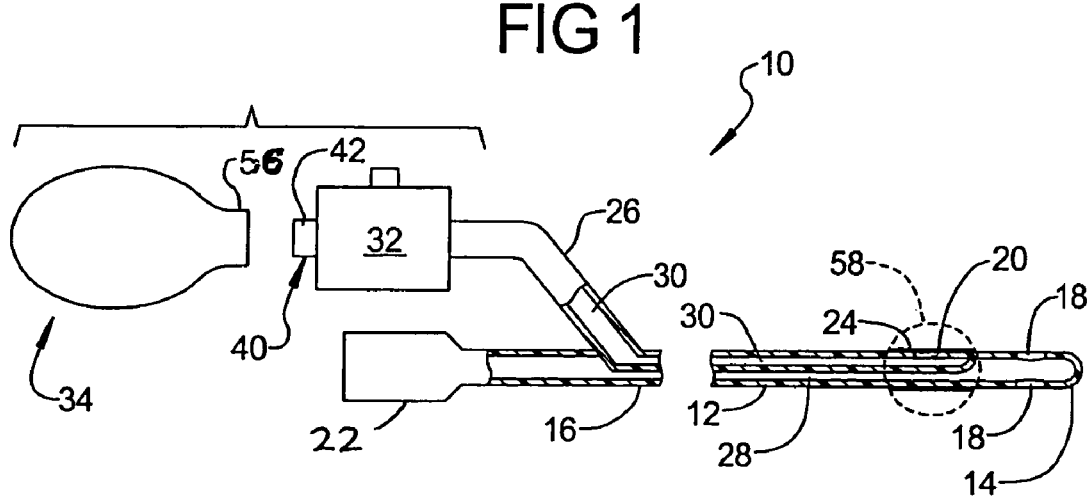
FIG. 1 is an exploded side view, partially in section, of a balloon catheter according to the present invention.

Referring to the drawings, FIG. 1 shows a balloon catheter system, generally indicated by the number 10. The balloon catheter system 10 is a conventional Foley-type catheter and comprises a relatively long and flexible tubular shaft 12 having a distal end or tip 14, a proximal end 16, a pair of drainage eyes 18 and an inflation port 20 proximate to the tip, a drainage funnel 22, a membrane 24 which is inflatable into a retention balloon 58, and a side conduit or arm 26. A drainage lumen 28 extends from the drainage eyes 18 to the funnel 22 and a small inflation lumen 30 extends from the inflation port 20 to the side arm 26.

As shown the balloon forming membrane 24 engirdles the catheter shaft 12 and is in covering relation about and with the inflation port 20. The membrane 24 is of a resilient material capable of expanding outwardly, when placed under fluid pressure, and form into a balloon. Conversely, the material of the membrane 24 will restore into its close form fitting relation with the shaft 12 when the fluid pressure is removed.

In the balloon catheter according to an embodiment of the present invention, a controllable closing device or control valve 32 and a squeeze bulb 34 having a reservoir filled with fluid to inflate the membrane 24 are integrated into the side arm 26. The control valve 32 can selectively close off, or open, the inflation lumen 30 Such closing can have at least two functions. First, it can provide an opportunity to remove or purge air present inside the balloon catheter prior to use, and then close off the balloon catheter. Second, it becomes possible to maintain the pressure in that section of the lumen connected to the balloon and in the balloon itself.

In a preferred embodiment, the closing device or control valve 32 is at the proximal end 16 of the catheter shaft 12 and connected in sealed relation thereto. The control valve 32 includes a housing 36, made of a material impermeable to fluids and having an interior chamber 38, a supply tube 40 having an inlet 42 and outlet 44, respectively, exterior to and interior of the chamber 38, and a generally planar closure or valve plate 46 having a circular shaped central opening 48. The interior diameters of the tubes 12 and 40 and the diameter of the central opening 48 are substantially the same. Further, the axes of the tubes 12 and 40 are coaxially aligned with one another and adapted to be placed in coaxial relation with the center of the central opening 48.

Figure 2:
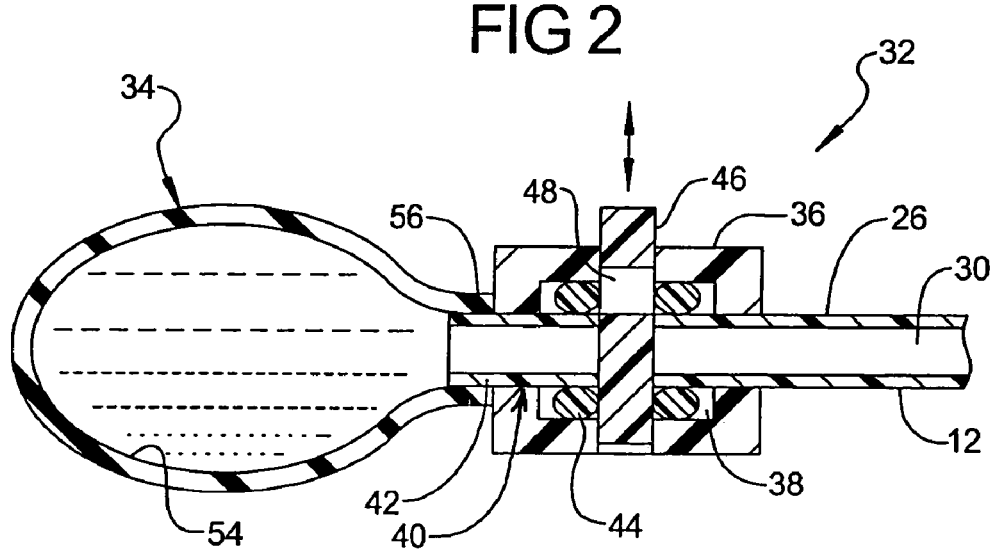
FIG. 2 is a section view of a squeeze bulb and fluid control valve of the catheter according to this invention, the control valve being in a closed position for preventing flow from or into a fluid reservoir of the squeeze bulb.
Figure 3:
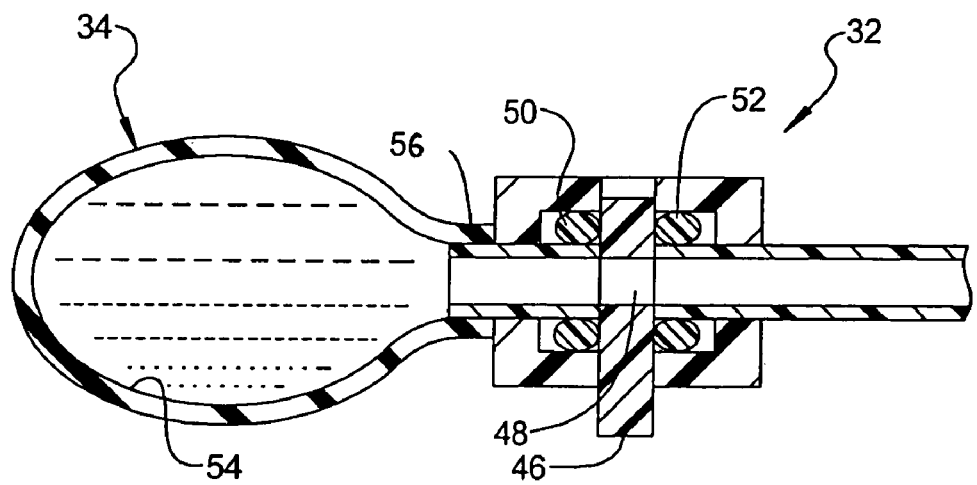
FIG. 3 is a section view of the squeeze bulb and control valve of FIG. 2, the valve being in the open position for permitting flow from or into the fluid reservoir of the squeeze bulb.

The valve plate 46 is mounted in the housing 36 for movement between first and second positions and in a direction that is transverse to a common center axis through the tubes 12 and 40. In the first position, as illustrated in FIG. 2, the central opening 48 of the plate is not aligned with the tubes 12 and 40 and the valve plate 46 prevents fluid from flowing between the tubes 12 and 40. In the second position, as illustrated in FIG. 3, the central opening 48 is aligned with the tubes 12 and 40 and the valve plate 46 permits fluid to flow between the tubes 12 and 40.

The valve plate 46 is in fluid sealed relation with the tubes 12 and 40 in either of the positions. As illustrated in FIGS. 2 and 3, an annular O-ring 50 seals the interface between the valve plate 46 and about the end 44 of the supply tube 40, and an O-ring 52 seals the interface between the valve plate 46 and about the proximal end 16 of the tube 12. So connected, the end faces of the tubes 12 and 40 are juxtaposed in sealed relation against the opposite planar faces of the valve plate 46.

According to this invention, the squeeze bulb 34 includes a central reservoir 54 and an attachment stub 56. The reservoir 54 is dimensioned to receive a suitable volume of fluid, and the stub 56 defines a fluid outlet, which is connected to the tube 40, thereby placing the fluid in the reservoir 54 in fluid communication with the inflation lumen 30 to suitably inflate the balloon. Depending on the application, the reservoir 54 may be filled with a suitable fluid medium, including a liquid, such as water or a saline solution, or air.

Preferably, the elements of the valve 32 and the squeeze bulb 34 are of a material impermeable to liquid. Additionally, the material of the squeeze bulb is resilient, and able to be collapsed by the action of a hand gripping manipulation, and yet firm to maintain shape as well as return to its original state. In one application, the squeeze bulb 34 is comprised of an elastomeric material, such as rubber, so as to yield easily to dispense balloon-inflating liquid and also to snap back and be restored to its original shape. Depending on the application, the squeeze bulb 34 is comprised of a high-density polyethylene.

The squeeze bulb 34 may be removably or non-removably secured to the end 42 of the supply tube 40. In either case, the attachment stub 56 is fitted to the inlet end portion of the supply tube 40.

In an aspect of this invention, the reservoir 54 is provided with a pre-measured amount of fluid and the squeeze bulb 34 is permanently affixed to the supply tube 40.

In another aspect of this invention, fluid is added to the reservoir 54 and the squeeze bulb 34 is then fitted to the supply tube.

In yet another aspect, the squeeze bulb 34 is dimensioned to receive a sufficient volume of air.

In a method of use, the catheter 10 is prepared, with the valve plate 46 placed in the closed position (FIG. 2), the reservoir 54 is filled as needed, and the squeeze bulb 34 is attached to the valve 32. The distal end 14 of the catheter shaft 12 is inserted into the urethra of a patient until the tip 14 at the distal end of the shaft 12 is disposed within the bladder. The valve plate 46 is pushed in a simple hand movement into the open position (FIG. 3), moving the opening 48 thereof into register with the tubes 12 and 40. The squeeze bulb 34 is then squeezed by the hand, causing the saline solution (or air) to be expelled from the reservoir 54, into and through the inflation lumen 30, and through the inflation port 20.

The fluid thus transmitted by hand squeezing of the squeeze bulb 34 causes the balloon material engirding the inflation port 20 to expand outwardly and form into a balloon shape 58, which shape engages the bladder wall of the patient to inhibit removal of the distal end of the catheter shaft 12 from the bladder.

The valve plate 48 is then moved into the first position (FIG. 2) to maintain the balloon 58 inflated.

Should removal of the catheter be desired, the valve plate 46 is moved into the fluid permitting position (FIG. 3), whereupon fluid flows outwardly of the balloon shape 58 and through the inflation lumen 30, causing the balloon to deflate and the balloon material to snap back into engagement with the tube 12.

While not shown as being understood by those skilled in the art, the drainage funnel 22 is appropriately connected to a urine collection bag.

As noted, the catheter according to this invention may be used in other therapeutic protocols.

The squeeze bulb is a "suction apparatus" and is adapted to remove inflating fluid from within the balloon 58 by suction, such as by creating a partial vacuum, and drawing the inflating fluid back into the reservoir to be used again.

The squeeze bulb or suction apparatus may be in the form of an aspirator, such as the aspirator 134 shown in FIG. 4, or the aspirator 234 shown in FIGS. 5 and 6. Each aspirator 134 and 234 is operated by hand, defines a fluid reservoir and fluid discharge port, and is configured for use with the control valve 32. The aspirator 134 and 234 may also be referred to as a bulb or pump and each is adapted to remove inflating fluid from within the balloon 58 by suction, such as by creating a partial vacuum, and drawing the inflating fluid back into the aspirator to be used again.

Turning to FIG. 4, the aspirator 134 is in the form of a one piece generally cylindrical bellows 60 of the pleated or accordion type, closed at the rearward end 62, open at the forward end 64, and forming a collapsible receptacle or reservoir 66 for storing a fluid for inflating the balloon 58. The forward end 64 forms a round neck that is adapted to mount onto the cylindrical neck 42 protruding from the control valve 32 and form a fluid sealed fitment therewith. The bellows 60 is formed of a succession of annular generally V-shaped folds or pleats 68 that enable the body thereof to axially compress and/or expand. An axial force placed on the bellows 60 forces the ends 62 and 64 towards and away from one another, depending on the direction of force applied.

The bellows 60 is preferably formed of a resilient material that remains flexible and enables the cylinder to move between an expanded state, when the reservoir is filled, and into a collapsed state, when expelling fluid through the port 42 and into the inflation lumen 30 to inflate the balloon 58. Preferably, the material is resilient and adapted to restore the bellows 60 to its original shape. While many materials are contemplated, a suitable material comprises rubber, an elastomer, and a high-density polyethylene.

Turning to FIGS. 5 and 6, the aspirator 234 is in the form of a one-piece cylindrical bellows 70 of the pleated or accordion type, closed at a rearward end 72, open at the forward end 74, and forming a collapsible receptacle or reservoir 76 for storing a fluid for inflating the balloon 58. The forward end 74 is adapted to fit to the cylindrical neck 42 of the supply tube 40 protruding from the control valve 32 and form a sealed closure thereabout.

The bellows 70 is formed of a succession of annular generally V-shaped folds or pleats 78 that enables the body of the aspirator 234 to axially compress. When an axial compressing force is placed on the ends 72 and 74 of the bellows 70, that forces the ends to move towards one another, the bellows is compressed (see FIG. 6).

According to this embodiment, the rearward and rearward ends 72 and 74 form generally flat circular end walls. An annular cup-like element 80 projects inwardly from the rearward end wall 72 and into the reservoir or chamber 76. The cup-like element 80 terminates in a mating end face 82 and forms an annular recess 84 between the pleats 78 and about the outer periphery of the cup-like element 80. A cylindrical sleeve 86 projects inwardly from the forward end wall 74 and into the chamber 76. The sleeve 86 terminates in an end face 88 and forms an annular recess 90 between the pleats 78 and about the outer periphery of the sleeve 86. The sleeve 86 is adapted to fit in fluid sealed relation about the neck 42.

Importantly, when the sleeve 86 is mounted to the neck 42, the inward end faces 43 and 88 of the neck 42 and the sleeve 86 combine to form a generally flat planar mating face 92 adapted to mate with the mating end face 82 of the cup-like element 80. The mating between the end faces 82 and 92 is much like the mating engagement of a suction cup with a flat surface. When the bellows 70 is compressed, the mating end face 82 of the cup-like element 80 is forced towards and against the mating end face 92 formed by the sleeve 86 and neck 42, pushing the air therebetween radially outwardly towards the annular recess 90, eliminating the pressure inside the cup 80 and creating a vacuum, which seals, retains, and holds the cup element 80 tightly against the mating face 92.

The materials of the aspirator 234 are the same as those of the aspirator 134.

Further, and important to this aspect of the invention, a coil spring 94 is disposed within the fluid receiving chamber 76. As shown, the coil spring 94 has opposite ends 96 and 98, respectively, seated against the forward and rearward end walls 72 and 74. The rearward and forward end portions of the coil spring 94, respectively, nest within the forward and rearward annular recesses 84 and 90 formed about the cup-like element 80 and sleeve 82.

As illustrated in FIG. 5, in operation, the valve plate 46 is positioned upwardly, moving the central opening 48 from alignment with the fluid passages of the tubes 12 and 40. The control valve 32 is in the closed position and prevents fluid flow therethrough and to or from the balloon. The chamber 76 is filled with fluid and the aspirator 234 is connected to the neck 42 of the control valve 32.

Referring to FIG. 6, substantially simultaneously, the valve plate 46 is manually pushed downwardly, causing the central opening 48 to be centered with the tubes 12 and 40 and the control valve to be in the open position, and the ends 72 and 74 moved towards one another. The bellows 70 and the coil spring 94 compress and fluid is discharged from the chamber 76, through the inflation lumen 30, and outwardly of the inflation port 20, causing the membrane 24 to inflate and a balloon 58 to be formed within the bladder.

Continued closing pressure is applied to the bellows 70, bringing the mating end faces 82 and 92 into mated relation, causing air therebetween to be evacuated and generating a retention vacuum between the mating faces 82 and 92. Substantially simultaneously, the valve plate 46 is closed, preventing fluid flow from the balloon and the retention vacuum creates a suction force that holds the bellows 70 in compressed relation.

When removal of the catheter is desired, the valve plate 46 is moved to the open position, whereupon the coil spring 94 will expand the bellows 70, fluids to be sucked, or withdrawn, from the balloon, and the balloon to deflate. The valve plate 46 is then moved into the closed position, preventing fluid to flow from the fluid chamber 76. The catheter is then prepared for reuse, as desired.

Although not shown in the drawing, it should be noted that either the squeeze bulb 34 or aspirator 134 and 234 may be provided with a sealed orifice to enable insertion of a syringe needle directly through the bulb and into the supply tube, thereby bypassing the bulb, depending on the exigencies of the situation.

Having described preferred embodiments of my invention it is obvious that the invention described above is susceptible to many variations, modifications and changes without departing from the spirit of the invention or the scope of the appended claims. It should be understood that the invention is not to be limited except as by the appended claims.

What I claim is:

1. A catheter assembly, comprising:
    an elongated catheter body including a hollow tube having proximal and distal ends, the distal end including a drainage eye for draining fluid from the distal end through the tube to the proximal end thereof, an inflation lumen extending from the proximal end thereof through at least a portion of the catheter body and terminating at a forward end portion of the body in an aperture for passing fluid outwardly from and into the lumen, and a balloon forming membrane secured in covering relation with the aperture, the membrane being radially expandable in response to positive pressure on fluid passed through the interior of the inflation lumen, a fluid regulating valve provided with an inlet and an outlet and a manually operable closure member, the outlet being fluidly connected to the aperture in the inflation lumen and the closure member mounted for movement transverse across the tube between open and closed positions, respectively, for permitting and preventing fluid to pass between the inlet and the outlet and into or from the inflation lumen, the valve including a fluid impermeable material housing and having an interior chamber, a supply tube having an inlet and outlet exterior to and interior of the chamber, a generally planar valve plate having a circular shaped central opening, the interior diameters of the tubes and the diameter of the central opening being substantially the same, the axes of the tubes being coaxially aligned with one another and in coaxial relation with the center of the central opening, and a manually operable aspirator pump fluidly connected to the inlet, said aspirator comprising a generally cylindrical bellows of the pleated type, having opposite ends and axially collapsible, and defining a variable volume hollow interior chamber.

2. The catheter assembly according to claim 1, further comprising a coil spring, said spring mounted in the interior chamber for biasing the opposite ends of the bellows in opposite axial directions whereby to axially expand the bellows.

3. The catheter assembly according to claim 2, wherein:
    said fluid regulating valve includes a valve housing having an interior for housing said closure member and said inlet forms a supply tube for connection to and communicating fluid from the aspirator to the interior of said valve housing, and the interior chamber of said aspirator pump includes opposite end walls that form, at least in part, mating end faces, wherein when the closure member of the control valve is in the closed position, the end faces are adapted to be manually pressed together in a manner to evacuate fluid between the mating end faces and form a suction cup like retention therebetween that sealingly mates and holds one end face to the other end face.

4. The catheter assembly according to claim 3, wherein said aspirator pump is removably connected, at least in part, to said supply tube and said fluid regulating valve.

5. The catheter assembly according to claim 3, wherein said aspirator pump is non-removably connected, at least in part, to said supply tube and said fluid regulating valve.

6. The catheter assembly according to claim 3, wherein said aspirator pump is comprised of a material that is resilient and flexible and impermeable to liquid penetration.

7. The catheter assembly according to claim 6, wherein said material is a self-restoring rubber, which will operate to restore the shape of the aspirator pump, once deformed, back into its original undeformed shape.

8. The catheter assembly according to claim 6, wherein said material is an elastomer, which will operate to restore the shape of the aspirator pump, once deformed, back into its original undeformed shape.

9. The catheter assembly according to claim 1, wherein:
said valve housing is comprised of a material that is impermeable to liquids and has opposed pairs of first and second endwalls, and
said closure member is planar and movable between and in generally parallel relation to the first end walls and between said open and closed positions by a hand operated pushing motion.

* * * * *